(12) United States Patent
Liniger et al.

(10) Patent No.: US 11,426,339 B2
(45) Date of Patent: Aug. 30, 2022

(54) ORGANIC COMPOUNDS

(71) Applicant: Givaudan SA, Vernier (CH)

(72) Inventors: Marc Liniger, Embrach (CH); Thierry Granier, Duebendorf (CH); Dominique Lelievre, Kindhausen (CH)

(73) Assignee: Givaudan SA, Vernier (CH)

( * ) Notice: Subject to any disclaimer, the term of this patent is extended or adjusted under 35 U.S.C. 154(b) by 145 days.

(21) Appl. No.: 17/050,615

(22) PCT Filed: May 15, 2019

(86) PCT No.: PCT/EP2019/062472
§ 371 (c)(1),
(2) Date: Oct. 26, 2020

(87) PCT Pub. No.: WO2018/210828
PCT Pub. Date: Nov. 22, 2018

(65) Prior Publication Data
US 2021/0045985 A1  Feb. 18, 2021

(30) Foreign Application Priority Data

May 15, 2018  (WO) ................. PCT/EP2018/062552
Nov. 12, 2018  (WO) ................. PCT/EP2018/080974

(51) Int. Cl.
| | | |
|---|---|---|
| *C11D 3/50* | (2006.01) | |
| *A61K 8/37* | (2006.01) | |
| *A61Q 13/00* | (2006.01) | |
| *A61Q 19/10* | (2006.01) | |
| *C07C 69/74* | (2006.01) | |
| *C11B 9/00* | (2006.01) | |

(52) U.S. Cl.
CPC ............... *A61K 8/37* (2013.01); *A61Q 13/00* (2013.01); *A61Q 19/10* (2013.01); *C07C 69/74* (2013.01); *C11B 9/0038* (2013.01)

(58) Field of Classification Search
CPC . A61K 8/36; A61K 8/37; A61Q 13/00; A61Q 19/10; C11B 9/0038; C07C 69/74
See application file for complete search history.

(56) References Cited

U.S. PATENT DOCUMENTS

| | | | |
|---|---|---|---|
| 3,952,034 A * | 4/1976 | Thompson | .............. C07C 67/38 560/207 |
| 4,397,789 A | 8/1983 | Boden et al. | |
| 4,485,019 A | 11/1984 | Boden et al. | |
| 4,755,502 A | 7/1988 | Sprecker et al. | |
| 4,824,707 A | 4/1989 | Spector | |
| 5,075,492 A * | 12/1991 | Keil | ........................ C07C 67/38 560/114 |
| 8,383,574 B2 | 2/2013 | Kotachi et al. | |
| 2011/0071070 A1 | 3/2011 | Kotachi et al. | |
| 2016/0326457 A1 | 11/2016 | Mishiro et al. | |
| 2020/0165539 A1 | 5/2020 | Lelievre et al. | |

FOREIGN PATENT DOCUMENTS

| | | | |
|---|---|---|---|
| DE | 3610049 | A1 | 10/1986 |
| EP | 1698684 | A1 | 9/2006 |
| EP | 2253695 | A1 | 11/2010 |
| JP | 40005699 | B * | 3/1965 |
| WO | 2004035017 | A1 | 4/2004 |
| WO | 2010120961 | A2 | 10/2010 |

OTHER PUBLICATIONS

International Search Report for International Application No. PCT/EP2019/062472 dated Jul. 8, 2019.
Written Opinion for International Application No. PCT/EP2019/062472 dated Jul. 8, 2019.
International Search Report for International Application No. PCT/EP2018/062552 dated Jul. 9, 2018.
Written Opinion for International Application No. PCT/EP2018/062552 dated Jul. 9, 2018.
International Search Report for International Application No. PCT/EP2018/080974 dated Jan. 24, 2019.
Written Opinion for International Application No. PCT/EP2018/080974 dated Jan. 24, 2019.
Albert Demonceau, et al., Novel Ruthenium-Based Catalyst Systems for the Ring-Opening Metathesis Polymerization of Low-Strain Cyclic Olefins, Macromolecules, Jun. 2, 1997, pp. 3127-3136, vol. 30, Issue 11, The American Chemical Society.
Maosheng Li, et al., Regio-/Stereoregular Glycine-Bearing Polymers from ROMP: Effect of Microstructures on Materials Performances, Macromolecules, Dec. 15, 2016, pp. 9415-9424, vol. 49, Issue 24, The American Chemical Society.
Fan et al, Identification of Aroma Compounds in Chinese "moutai" and "Lanjiu" Liquors by Normal Phase Liquid Chromatography Fractionation Followed by Gas Chromatography/Olfactometry, 2012, 311-338 (Year: 2012).
Jutta Reiners, et al., Odorants of Virgin Olive Oils with Different Flavor Profiles, J. Agric. Food Chem., Jun. 26, 1998, pp. 2754-2763, vol. 46, American Chemical Society.
Laura Franitza, et al., Characterization of the Key Aroma Compounds in Two Commercial Rums by Means of the Sensomics Approach, J. Agric. Food Chem., Dec. 30, 2015, pp. 637-645, vol. 64, American Chemical Society.

* cited by examiner

*Primary Examiner* — John R Hardee

(74) *Attorney, Agent, or Firm* — Curatolo, Sidoti & Trillis Co., LPA; Salvatore A. Sidoti; Floyd Trillis, III

(57) ABSTRACT

The present invention relates to ethyl cyclooct-3/4-ene-1-carboxylates, and to a process of making the same. The invention further refers to flavour and fragrance compositions comprising them.

7 Claims, No Drawings

ORGANIC COMPOUNDS

CROSS REFERENCE TO RELATED APPLICATIONS

This application is a national stage application of International Application No. PCT/EP2019/062472, filed 15 May 2019, which claims priority from International Application No. PCT/EP2018/080974, filed 12 Nov. 2018 and International Application No. PCT/EP2018/062552, filed 15 May 2018, all of which applications are incorporated herein by reference in their entireties.

The present invention relates to fruity esters. In particular the present invention relates to ethyl cyclooct-3/4-ene-1-carboxylates possessing fruity overripe facets. The invention furthermore refers to methods of their production, and to flavour and fragrance compositions containing these.

A very common class of fragrance ingredient is the ester. Esters are found in the essential oils of many plants and are known for their sweet, fruity odor. As a result, they are a popular choice for fragrance compositions. Typical examples of popular fragrance esters include benzyl acetate (1), bornyl acetate ((2); 1,7,7-trimethylbicyclo[2.2.1]heptan-2-yl acetate), 2-tert-butyl-cyclohexylacetate ((3) Agrumex™), octahydro-4,7-methano-3aH-indene-3a-carboxylic acid, ethyl ester ((4) Fruitate™), and 1,3-cyclohexadiene-1-carboxylic acid, 2,6,6-trimethyl-, ethyl ester ((5) Ethyl Safranate™)

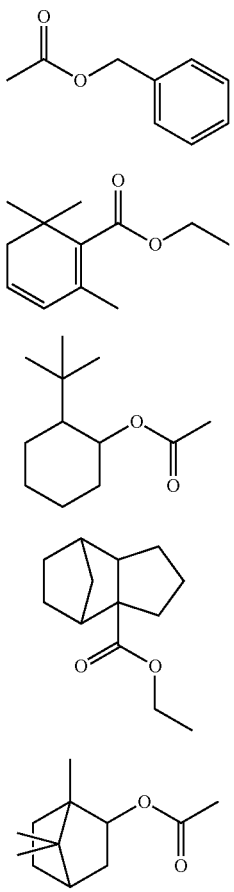

All of these do have in common that they have either a cyclohexyl backbone or a polycyclic backbone.

Surprisingly, we have now found a new class of esters with a cyclooctene backbone possessing fruity over ripe facet, which is much thought of in the flavour and fragrance industry. Compounds possessing fruity over ripe odor notes are of particular interest since these odor profiles contribute to the naturality impression.

Ethyl cyclooctenecarboxylates are known as intermediates for the synthesis of, e.g., polymers (as one example one may cited Demonceau, A. et al., *Macromolecules* 1997, 30, 3127). However, according to the best of our knowledge, organoleptic properties of such compounds are not set forth.

There is provided in a first embodiment the use as flavour or fragrance of a compound of formula (I)

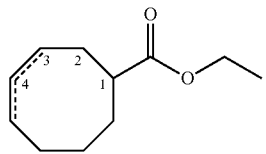

(I)

wherein one of the dotted lines represents together with the carbon-carbon bond a single bond and the other dotted line represents together with the carbon-carbon bond a double bond.

As a specific example of compounds of formula (I), one may cite ethyl (Z)-cyclooct-4-ene-1-carboxylate which possesses a very clean, natural, pleasant olfactive profile, where the "fruity over ripe" relates olfactively to real, natural, fresh berries, like raspberries in particular, but also kiwi, banana, apple and pineapple in general.

As a further example of compounds of formula (I), one may cite ethyl (Z)-cyclooct-3-ene-1-carboxylate which possesses a relatively natural, pleasant olfactive profile, but slightly unbalanced by the slight chemical, green, artificial facet.

The compounds of formula (I) may be used alone, or in combination with known odorant molecules selected from the extensive range of natural products, and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art.

As used herein, "carrier material" means a material which is practically neutral from a odorant point of view, i.e. a material that does not significantly alter the organoleptic properties of odorants.

The term "auxiliary agent" refers to ingredients that might be employed in a fragrance composition for reasons not specifically related to the olfactive performance of said composition. For example, an auxiliary agent may be an ingredient that acts as an aid to processing a fragrance ingredient or ingredients, or a composition containing said ingredient(s), or it may improve handling or storage of a fragrance ingredient or composition containing same. It might also be an ingredient that provides additional benefits such as imparting color or texture. It might also be an ingredient that imparts light resistance or chemical stability to one or more ingredients contained in a fragrance composition. A detailed description of the nature and type of adjuvants commonly used in fragrance compositions containing same cannot be exhaustive, but it has to be mentioned that said ingredients are well known to a person skilled in the art.

As used herein, 'fragrance composition' means any composition comprising the compound of formula (I) and a base material, e.g. a diluent conventionally used in conjunction with odorants, such as diethyl phthalate (DEP), dipropylene glycol (DPG), isopropyl myristate (IPM), pentane-1,2-diol, triethyl citrate (TEC) and alcohol (e.g. ethanol). Optionally, the composition may comprise an anti-oxidant adjuvant. Said anti-oxidant may be selected from Tinogard® TT (BASF), Tinogard® Q (BASF), Tocopherol (including its isomers, CAS 59-02-9; 364-49-8; 18920-62-2; 121854-78-2), 2,6-bis(1,1-dimethylethyl)-4-methylphenol (BHT, CAS 128-37-0) and related phenols, hydroquinones (CAS 121-31-9).

The following list comprises examples of known odorant molecules, which may be combined with the compounds of formula (I):

essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil and/or ylang-ylang oil;

alcohols, e.g. cinnamic alcohol ((E)-3-phenylprop-2-en-1-ol); cis-3-hexenol ((Z)-hex-3-en-1-ol); citronellol (3,7-dimethyloct-6-en-1-ol); dihydro myrcenol (2,6-dimethyloct-7-en-2-ol); Ebanol™ ((E)-3-methyl-5-(2,2,3-trimethylcyclopent-3-en-1-yl)pent-4-en-2-ol); eugenol (4-allyl-2-methoxyphenol); ethyl linalool ((E)-3,7-dimethylnona-1,6-dien-3-ol); farnesol ((2E,6Z)-3,7,11-trimethyldodeca-2,6,10-trien-1-ol); geraniol ((E)-3,7-dimethylocta-2,6-dien-1-ol); Super Muguet™ ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol™ (3,7-dimethyloct-6-en-1-ol); Sandalore™ (3-methyl-5-(2,2,3-trimethylcyclopent-3-en-1-yl)pentan-2-ol); terpineol (2-(4-methylcyclohex-3-en-1-yl)propan-2-ol); or Timberol™ (1-(2,2,6-trimethylcyclohexyl)hexan-3-ol); 2,4,7-trimethylocta-2,6-dien-1-ol, and/or [1-methyl-2(5-methylhex-4-en-2-yl)cyclopropyl]-methanol;

aldehydes and ketones, e.g. anisaldehyde (4-methoxybenzaldehyde); alpha amyl cinnamic aldehyde (2-benzylideneheptanal); Georgywood™ (1-(1,2,8,8-tetramethyl-1,2,3,4,5,6,7,8-octahydronaphthalen-2-yl) hethanone); Hydroxycitronellal (7-hydroxy-3,7-dimethyloctanal); Iso E Super® (1-(2,3,8,8-tetramethyl-1,2,3,4,5,6,7,8-octahydronaphthalen-2-yl) hethanone); Isoraldeine® ((E)-3-methyl-4-(2,6,6-trimethylcyclohex-2-en-1-yl)but-3-en-2-one); Hedione® (methyl 3-oxo-2-pentylcyclopentaneacetate); 3-(4-isobutyl-2-methylphenyl)propanal; maltol; methyl cedryl ketone; methylionone; verbenone; and/or vanillin;

ether and acetals, e.g. Ambrox® (3a,6,6,9a-tetramethyl-2,4,5,5a,7,8,9,9b-octahydro-1H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); and/or Spirambrene® (2',2',3,7,7-pentamethylspiro[bicyclo[4.1.0]heptane-2,5'-[1,3]dioxand]);

esters and lactones, e.g. benzyl acetate; cedryl acetate ((1S,6R,8aR)-1,4,4,6-tetramethyloctahydro-1H-5,8a-methanoazulen-6-yl acetate); γ-decalactone (6-pentyltetrahydro-2H-pyran-2-one); Helvetolide® (2-(1-(3,3-dimethylcyclohexyl)ethoxy)-2-methylpropyl propionate); γ-undecalactone (5-heptyloxolan-2-one); and/or vetiveryl acetate ((4,8-dimethyl-2-propan-2-ylidene-3,3a,4,5,6,8a-hexahydro-1H-azulen-6-yl) acetate);

macrocycles, e.g. Ambrettolide ((Z)-oxacycloheptadec-10-en-2-one); ethylene brassylate (1,4-dioxacycloheptadecane-5,17-dione); and/or Exaltolide® (16-oxacyclohexadecan-1-one); and heterocycles, e.g. isobutylquinoline (2-isobutylquinoline).

The compound according to formula (I) may be used in a broad range of fragranced articles, e.g. in any field of fine and functional perfumery, such as perfumes, air care products (including air care products for delivery a volatile product to an ambient environment using a permeable or porous membrane-based dispensing devices as disclosed, e.g. in WO2010120961 or U.S. Pat. No. 4,824,707), household products, laundry products, body care products and cosmetics. The compound can be employed in widely varying amounts, depending upon the specific article and on the nature and quantity of other odorant ingredients. The proportion is typically from 0.0001 to 3 weight percent of the article. In one embodiment, the compound of the present invention may be employed in a fabric softener in an amount from 0.001 to 0.3 weight percent (e.g. 0.01 to 0.1 including 0.05 weight %). In another embodiment, the compound of formula (I) may be used in fine perfumery in amounts from 0.001 to 30 weight percent (e.g. up to about 10 or up to 20 weight percent), more preferably between 0.01 and 5 weight percent. However, these values are given only by way of example, since the experienced perfumer may also achieve effects or may create novel accords with lower or higher concentrations.

In one embodiment there is provided a fragranced article comprising an acceptable amount of at least one compound of formula (I), a mixture thereof. For example, the fragrance article may comprise 0.000001 weight % to 90 weight % (including 0.00001 weight %; 0.0001 weight %, 0.001 weight %, 0.01 weight %, 0.05 weight %, 0.1 weight %, 0.5 weight %, 1 weight %, 5 weight %, 8 weight %, 10 weight %, 15 weight %, 20 weight %, 25 weight %, 30 weight %, 50 weight %, 60 weight %, 65 weight %) based on the total amount of the article.

The compounds as described hereinabove may be employed in a consumer product base simply by directly mixing the compound of formula (I), or a fragrance composition comprising the compound of formula (I), or a mixture thereof, with the consumer product base, or it may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, and then mixed with the consumer product base.

Thus, the invention additionally provides a method of manufacturing a fragranced article, comprising the incorporation of a compound of formula (I), as a fragrance ingredient, either by directly admixing the compound to the consumer product base or by admixing a fragrance composition comprising the compound of formula (I), which may then be mixed with a consumer product base, using conventional techniques and methods. Through the addition of an olfactory acceptable amount of the compound of the present invention as hereinabove described the odor notes of a consumer product base will be improved, enhanced, or modified.

Thus, the invention furthermore provides a method for improving, enhancing or modifying a consumer product base by means of the addition thereto of an olfactorily acceptable amount of the compound of formula (I).

The invention also provides a fragranced article comprising:
a) as odorant the compound of formula (I), or a mixture thereof; and
b) a consumer product base.

As used herein, 'consumer product base' means a composition for use as a consumer product to fulfill specific actions, such as cleaning, softening, and caring or the like. Examples of such products include fine perfumery, e.g. perfume and eau de toilette; fabric care, household products and personal care products such as cosmetics, laundry care detergents, rinse conditioner, personal cleansing composition, detergent for dishwasher, surface cleaner; laundry products, e.g. softener, bleach, detergent; body-care products, e.g. shampoo, shower gel; air care products (includes products that contain preferably volatile and usually pleasant-smelling compounds which advantageously can even in very small amounts mask unpleasant odors). Air fresheners for living areas contain, in particular, natural and synthetic essential oils such as pine needle oils, citrus oil, eucalyptus oil, lavender oil, and the like, in amounts for example of up to 50% by weight. As aerosols they tend to contain smaller amounts of such essential oils, by way of example less than 5% or less than 2% by weight, but additionally include compounds such as acetaldehyde (in particular, <0.5% by weight), isopropyl alcohol (in particular, <5% by weight), mineral oil (in particular, <5% by weight), and propellants.

Cosmetic products include:
(a) cosmetic skincare products, especially bath products, skin washing and cleansing products, skincare products, eye makeup, lip care products, nail care products, intimate care products, foot care products;
(b) cosmetic products with specific effects, especially sunscreens, tanning products, de-pigmenting products, deodorants, antiperspirants, hair removers, and shaving products;
(c) cosmetic dental-care products, especially dental and oral care products, tooth care products, cleaners for dental prostheses, adhesives for dental prostheses; and
(d) cosmetic hair care products, especially hair shampoos, hair care products, hair setting products, hair-shaping products, and hair coloring products.

This list of products is given by way of illustration, and is not to be regarded as being in any way limiting.

The compounds of formula (I) may, for example, be prepared by alkoxycarbonylation or esterification under conditions known to the person skilled in the art.

The invention is now further described with reference to the following non-limiting examples. These examples are for the purpose of illustration only and it is understood that variations and modifications can be made by one skilled in the art.

All products were purified after work-up by either flash chromatography (FC) using Tsingdao Haiyang Chemical silica gel (200±300 mesh) and silica gel Merck grade (60 Å) or distillation. Unless otherwise noted, a mixture of pentane:MTBE (10:1) was used as eluent. $^1H$ and $^{13}C$ NMR spectra were measured in $CDCl_3$, referenced to the residual hydrogen signal of the deuterated solvent ($^1H$ 7.26 ppm, $^{13}C$ 77.0 ppm) and are reported as follows: chemical shifts (δ ppm), coupling constants J in Hz. GC-MS analyses were run on a MSD5975 mass spectrometer and are reported as m/z list (relative intensity). Odor description refers to the odor of the isomeric mixture of the compounds unless otherwise indicated.

EXAMPLE 1 ethyl (Z)-cyclooct-4-ene-1-carboxylate

An autoclave was charged with $PdCl_2$ (319 mg, 2 mol %), $PPh_3$ (1.42 g, 6 mol %), 1,5-cyclooctadiene (15.6 g, 144 mmol, 1.6 equiv) and EtOH (4.15 g, 90 mmol, 1.0 equiv). The reaction mixture was then sealed, flushed 3 times with CO and stirred at 100° C. under an atmosphere of CO (45 bar) for 5 h. The crude product was purified by Kugelrohr distillation (150° C./0.01 mbar) and fractional distillation over a 2 cm Vigreux column (bp 73° C. at 0.08 mbar) to afford ethyl (Z)-cyclooct-4-ene-1-carboxylate (7.5 g, 46% yield) as a colorless liquid.

$^1H$ NMR (400 MHz, $CDCl_3$): δ 5.67 (dt, J=10.5, 7.3 Hz, 1H), 5.67-5.57 (m, 1H), 4.08 (q, J=7.1 Hz, 2H), 2.48-2.29 (m, 2H), 2.19-1.95 (m, 4H), 1.88-1.79 (m, 1H), 1.77-1.50 (m, 3H), 1.45-1.31 (m, 1H), 1.22 (t, J=7.2 Hz, 3H) ppm. $^{13}C$ NMR (101 MHz, $CDCl_3$): δ 177.6, 130.5, 129.5, 60.1, 43.3, 31.6, 29.4, 27.8, 25.8, 24.1, 14.2 ppm. GC-MS (EI) m/z (%): 182 (20, [M]$^+$), 109 (87), 108 (66), 94 (26), 93 (27), 79 (44), 67 (100), 55 (48), 54 (31), 41 (43), 39 (30). bp 73° C. (0.08 mbar).

Odor description: a very clean, natural, pleasant olfactive profile, where the "fruity over ripe" relates olfactively to real, natural, fresh berries, like raspberries in particular, but also kiwi, banana, apple and pineapple in general

EXAMPLE 2 ethyl (Z)-cyclooct-3-ene-1-carboxylate

A solution of sodium hypobromite was prepared as follows: Bromine (23.3 mL, 3 equiv) was added at 5-10° C. to a solution of NaOH (79 g, 13 equiv) in water (230 mL). After stirring for 15 min, the solution was diluted with cold dioxane (92 mL). To a solution of (Z)-1-(cyclooct-3-en-1-yl)ethan-1-one (23.0 g, 151 mmol, 1.0 equiv, prepared according to Granier, T. et aL, WO 200403501) in dioxane (230 mL) and water (115 mL) was added dropwise at 0° C. a freshly prepared solution of NaOBr (prepared as described above) at such a rate that the reaction temperature did not exceed 15° C. After stirring at room temperature for 1 h, the reaction mixture was diluted with sat. aq. $NaS_2O_3$ (50 mL) and MTBE (70 mL). The layers were separated and the organic layer was extraced with 2M NaOH (2×). The organic layer was discarded. The aqueous layer was acidified with conc. HCl and extracted with MTBE (2×). The combined organic extracts were dried over $MgSO_4$, filtered and concentrated under reduced pressure to give crude (Z)-cyclooct-3-ene-1-carboxylic acid (20 g).

$^1H$ NMR (400 MHz, $CDCl_3$): δ 10.7 (brs, 1H), 5.77 (dt, J=10.4, 8.0 Hz, 1H), 5.63 (dt, J=10.5, 7.9 Hz, 1H), 2.60-2.34 (m, 3H), 2.26-2.06 (m, 2H), 1.89-1.63 (m, 3H), 1.61-1.43 (m, 3H) ppm. $^{13}C$ NMR (101 MHz, $CDCl_3$): δ 182.4, 132.3, 127.1, 44.8, 29.2, 27.9, 26.8, 25.9, 24.5 ppm. GC-MS (EI) m/z (%): 154 (17, [M]$^+$), 136 (33), 109 (63), 82 (29), 81 (35), 79 (43), 67 (100), 55 (52), 54 (49), 41 (64.0), 39 (48).

A solution of crude (Z)-cyclooct-3-ene-1-carboxylic acid (2.0 g, 13.0 mmol, 1.0 equiv) and para-toluenesulfonic acid monohydrate (247 mg, 1.30 mmol, 10 mol %) in EtOH (15 mL) was refluxed for 14 h and concentrated under reduced pressure. The crude was purified by Kugelrohr distillation (140° C./0.04 mbar) to afford ethyl (Z)-cyclooct-3-ene-1-carboxylate (1.7 g, 72%, contains 7% of ethyl cyclooct-1-ene-1-carboxylate) as a colorless liquid.

(Z)-cyclooct-3-ene-1-carboxylate: $^1$H NMR (400 MHz, CDCl$_3$): δ 5.71 (dt, J=10.5, 7.8 Hz, 1H), 5.59 (dt, J=10.4, 7.8 Hz, 1H), 4.09 (q, J=7.1 Hz, 2H), 2.51-2.39 (m, 2H), 2.36-2.12 (m, 2H), 2.12-2.01 (m, 1H), 1.84-1.59 (m, 3H), 1.59-1.38 (m, 3H), 1.22 (t, J=7.1 Hz, 3H) ppm. $^{13}$C NMR (101 MHz, CDCl$_3$): δ 175.8, 131.9, 127.4, 60.0, 45.0, 29.1, 28.2, 27.1, 25.8, 24.3, 14.2 ppm. GC-MS (El) m/z (%):182 (21, [M]$^+$), 109 (76), 108 (60), 94 (31), 93 (25), 79 (48), 67 (100), 55 (47), 41 (43), 39 (33), 29 (40).

ethyl cyclooct-1-ene-1-carboxylate: GC-MS (El) m/z (%): 182 (39, [M]$^+$), 137 (47), 109 (72), 108 (55), 81 (35), 79 (46), 67 (100), 55 (47), 53 (37), 41 (48).

Odor description (ethyl (4-cyclooct-3-ene-1-carboxylate): still a relatively natural, pleasant olfactive profile, but slightly unbalanced by the slight chemical, green, artificial facet Odor description (ethyl cyclooct-1-ene-1-carboxylate): mainly perceived as chemical, plastic, with some berry, aromatic, slightly green facets: about 400 times weaker than the main constituent (ethyl (Z)-cyclooct-3-ene-1-carboxylate)

EXAMPLE 3 (COMPARISON)

ethyl (Z)-cyclooct-2-ene-1-carboxylate

A solution of (Z)-cyclooct-2-ene-1-carboxylic acid (8.64 g, 56.0 mmol, 1.0 equiv, prepared according to Li, M. et al., *Macromolecules* 2016, 49, 9415) and para-toluenesulfonic acid monohydrate (1.07 g, 5.60 mmol, 10 mol %) in EtOH (60 mL) was refluxed for 7 h using a Dean-Stark trap. Since the reaction mixture still contained some starting material, an additional amount of para-toluenesulfonic acid monohydrate (0.48 g, 2.52 mmol, 4.5 mol %) was added and refluxing was continued for 16 h. The reaction mixture was diluted with 2M aq. NaOH (60 mL), water and MTBE. The layers were separated and the aqueous layer was extracted with MTBE (2×80 mL). The combined organic extracts were dried over MgSO$_4$, filtered and concentrated under reduced pressure to give a crude product (4.27 g). The crude was purified by column chromatography (pentane/MTBE 50:1) and Kugelrohr distillation (90° C./0.04 mbar) to afford ethyl (Z)-cyclooct-2-ene-1-carboxylate (2.03 g, 20% yield, contains 8% of ethyl cyclooct-1-ene-1-carboxylate) as a colorless liquid. $^1$H NMR (400 MHz, CDCl$_3$): δ 5.80-5.71 (m, 1H), 5.67 (ddd, J=10.5, 8.6, 1.1 Hz, 1H), 4.14 (q, J=7.1 Hz, 2H), 3.48-3.37 (m, 1H), 2.23-2.03 (m, 2H), 1.97-1.84 (m, 1H), 1.75-1.62 (m, 2H), 1.62-1.51 (m, 3H), 1.49-1.28 (m, 2H), 1.25 (t, J=7.1 Hz, 3H). $^{13}$C NMR (101 MHz, CDCl$_3$): δ 175.5, 131.0, 127.7, 60.4, 42.7, 33.3, 29.1, 26.5, 26.4, 25.2, 14.2 ppm. GC-MS (El) m/z (%): 182 (13, [M]$^+$), 109 (58), 108 (38), 94 (23), 81 (24), 79 (30), 67 (100), 55 (35), 41 (36), 39 (24), 29 (33).

About 10 times weaker than ethyl (Z)-cyclooct-4-ene-1-carboxylate and ethyl (Z)-cyclooct-3-ene-1-carboxylate, both of which are similar not only with regard to the odor profile but also in odor strength.

Odor description: mainly perceived as chemical, green, artificial with a green, coniferous aspect. Overall, this relates to chemical, artificial, and results as unpleasant and unwanted olfactive character.

EXAMPLE 4

Fruity Gourmand Fragrance Composition Suitable for Shower Gel

| Compound/Ingredient | parts by weight 1/1000 |
|---|---|
| CIS-3-HEXENYL ACETATE | 9 |
| ACETOPHENONE (1-PHENYL-ETHANONE) | 5 |
| DODECANAL @10% TEC | 5 |
| CINNAMIC ALDEHYDE (3-PHENYL-2-PROPENAL) | 23 |
| METHYL ANTHRANILATE (METHYL 2-AMINOBENZOATE) | 4 |
| ETHYLENE BRASSYLATE (1,4-DIOXACYCLOHEPTADECANE-5-17-DIONE) | 124 |
| BUCHU LEAF OIL | 5 |
| ETHYL BUTYRATE | 20 |
| ETHYL HEXANOATE | 1 |
| CARVONE LAEVO (L-2-METHYL-5-ISOPROPENYL-2-CYCLOHEXENONE) | 40 |
| CYCLAL C (2,4-DIMETHYL-3-CYCLOHEXENE-1-CARBALDEHYDE) | 20 |
| DAMASCENONE (1-(2,6,6-TRIMETHYL-1,3-CYCLOHEXADIENE-1-YL)-2-BUTENE-1-ONE) | 20 |
| DAMASCONE ALPHA (1-(2,6,6-TRIMETHYL-2-CYCLOHEXEN-1-YL)-2-BUTEN-1-ONE) | 20 |
| DAMASCONE BETA (1-(2,6,6-TRIMETHYL-1-CYCLOHEXEN-1-YL)-2-BUTEN-1-ONE) | 17 |
| ETHYL MALTOL (3-HYDROXY-2-ETHYL-4H-PYRAN-4-ONE) | 50 |
| STRAWBERRY PURE (ETHYL 3-PHENYL-2,3-EPOXYBUTANOATE) | 10 |
| FRUCTONE (ETHYL 2-METHYL-1,3-DIOXOLANE-2-ACETATE) | 10 |
| HEDIONE (METHYL 3-OXO-2-PENTYLCYCLOPENTANEACETATE) | 100 |
| HEXENOL-3-CIS | 34 |
| METHYL 2-METHYLBUTYRATE | 2 |
| METHYL OCTYNE CARBONATE (METHYL 2-NONYNOATE) | 4 |
| ORANGE OIL | 200 |
| PEACH PURE (4-UNDECANOLIDE) | 20 |
| ETHYL PELARGONATE (ETHYL NONANOATE) | 1 |
| ETHYL PROPIONATE | 1 |
| UNDECAVERTOL (4-METHYL-3-DECEN-5-OL) | 10 |
| VANILLIN (4-HYDROXY-3-METHOXYBENZALDEHYDE) | 65 |
| DIPROPYLEN GLYCOLE (DPG) | 180 |
| Total: | 1000 |

By replacing 18 parts of DPG of the accord above with ethyl (Z)-cyclooct-4-ene-1-carboxylate the overall top note character shifts towards a natural, juicy, over ripe, pleasant fruity, berry, strawberry character both on neat and in use (i.e. when accord is applied @ 0.1% in shower gel).

By replacing 18 parts of DPG of the accord above with ethyl (Z)-cyclooct-3-ene-1-carboxylate the overall top note character shifts towards a juicy, over ripe, fruity, berry, strawberry character both on neat and in use (i.e. when accord is applied @ 0.1% in shower gel), with a slight green, artificial facet.

The invention claimed is:

1. A method comprising utilizing a compound of formula (I)

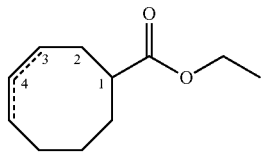

wherein one of the dotted lines represents together with the carbon-carbon bond a single bond and the other dotted line represents together with the carbon-carbon bond a double bond;

as flavor or fragrance, the method comprising mixing the compound of formula (I) with a consumer product base, or admixing a composition comprising the compound of formula (I) and mixing with a consumer product base.

2. Ethyl cyclooct-3-ene-1-carboxylate.

3. A fragrance composition comprising as odorant a compound of formula (I) as defined in claim 1, or a mixture thereof, and a base material.

4. A fragranced article comprising as odorant a compound of formula (I) as defined in claim 1, and a consumer product base.

5. The fragranced article according to claim 4, wherein the consumer product base is selected from the group consisting of fine fragrance, household products, laundry products, body care products, cosmetic products, air care products and combinations thereof.

6. A method of improving, enhancing or modifying a consumer product base comprising adding to the consumer product base an olfactory acceptable amount of a compound selected from the group consisting of ethyl cyclooct-3-ene-1-carboxylate, ethyl cyclooct-4-ene-1-carboxylate, and mixtures thereof.

7. The method according to claim 6, wherein the consumer product base is selected from the group consisting of fine fragrance, household products, laundry products, body care products, cosmetic products, air care products and combinations thereof.

* * * * *